United States Patent [19]

Stärk

[11] 3,930,953

[45] Jan. 6, 1976

[54] GLUCOSE OXIDASE POOR IN CATALASE AND PROCESS FOR OBTAINING IT

[75] Inventor: Josef Stärk, Marburg, Lahn, Germany

[73] Assignee: Behringwerke Aktiengesellschaft, Marburg, Lahn, Germany

[22] Filed: Feb. 15, 1974

[21] Appl. No.: 443,149

[30] Foreign Application Priority Data
Feb. 17, 1973  Germany............................ 2308013

[52] U.S. Cl................................. 195/62; 195/66 R
[51] Int. Cl.²........................................ C07G 7/028
[58] Field of Search............................ 195/62, 66 R

[56]  References Cited
UNITED STATES PATENTS

| 3,468,760 | 9/1969 | Joss................................... | 195/66 B |
| 3,645,851 | 2/1972 | Bergmeyer et al................ | 195/66 R |

Primary Examiner—Lionel M. Shapiro
Attorney, Agent, or Firm—Curtis, Morris & Safford

[57]  ABSTRACT

Glucose oxidase poor in catalase containing more than 250 U/mg of protein of glucose oxidase activity and less than 0.1 U/mg of protein of catalase activity and its manufacture by precipitating a prepurified glucose oxidase composition with a water soluble salt of an acridine base and subsequent chromatography on a cation exchanger and an anion exchanger.

7 Claims, No Drawings

GLUCOSE OXIDASE POOR IN CATALASE AND PROCESS FOR OBTAINING IT

The present invention relates to a glucose oxidase poor in catalase and a process for obtaining it.

The glucose oxidase poor in catalase of the invention is obtained from prepurified glucose oxidase.

It has been proposed in prior processes to isolate glucose oxidase from molds. The greatest number of these substances are crude products. There are also purer glucose oxidases available in commerce. They contain, however, about 10 units catalase per about 250 units glucose oxidase. It is not known how to prepare these substances.

It was shown that a glucose oxidase devoid of or at least poor in catalase can be used as growth inhibiting agent for tumor cells.

The glucose oxidase poor in catalase is characterized by the fact that its glucose oxidase activity is more than 250 units/mg of protein and its catalase activity less than 0.1 units/mg of protein.

The process for obtaining glucose oxidase poor in catalase is characterized by the fact that prepurified glucose oxidase compositions are precipitated with water-soluble salts of acridine bases, preferably diaminoethoxyacridine lactate and purified by chromatography using cation and anion exchangers. The process for obtaining glucose oxidase poor in catalase is, moreover, characterized by the fact that the starting materials are prepurified glucose oxidase compositions of molds, preferably *Aspergillus niger* or *Penicillium notatum*.

The preparation of glucose oxidase poor in catalase according to the invention is based on glucose oxidase compositions available in commerce. Those compositions are generally obtained by fermentation using corresponding micro organisms, such as *Aspergillus niger*. The glucose oxidase activity of these compositions is about 10 to 20 units/mg of protein and their catalase activity 1 unit/mg of protein or more.

Such a composition is purified, according to the invention, in an aqueous solution. A suitable solvent is a usual buffer solution, for example, a phosphate buffer solution, however, salt solutions, for example, sodium chloride or sodium phosphate solutions may also be used. The glucose oxidase is dissolved in this solvent to yield a solution of about 5 to 20 %. Low-molecular weight contaminations may be eliminated by dialyzing the solution against the pure solvent. The pH of the solution is preferably neutral to slightly acid, i.e., within the range of from about 7 to 4.

The glucose oxidase is precipitated from that solution with an aqueous solution of diaminoethoxyacridine lactate of about 2 to 10 %. It is applied in such an amount that about 0.5 to 2 mg of diaminoethoxyacridine lactate are used per 10 mg of protein of the glucose oxidase solution.

After mixing the two solutions it is useful to allow the mixture to dwell for about 12 to 24 hours at low temperature (0°C to room temperature), whereupon a diaminoethoxyacridine lactate protein complex containing the glucose oxidase precipitates. The complex is isolated by suitable measures, such as decanting, filtering or centrifuging.

The glucose oxidase is set free from the sediment so obtained by treating it with an aqueous chloride solution for which alkali metal and alkaline-earth metal chlorides are suitable and sodium chloride is preferred. A 2 to 10 % concentration of the solution is suitable, an about 5 % solution is preferred. The chloride solution is applied in an amount of about 25 to 50 ml per 10 g of the glucose oxidase initial product.

The chloride of the acridine base sparingly soluble which is obtained in this reaction is separated from the solution containing the glucose oxidase by usual methods, such as decanting, filtering or centrifuging. If desired, purification can be effected a second time by dialysis.

The following chromatography is effected using at first an acid ion exchanger and then a basic one. Especially effective are cation exchangers having functional sulfoethyl groups and anion exchangers having functional diethylamino groups. The adsorption at the ion exchangers occurs at a temperature ranging from 0°C to room temperature and at a pH ranging from 3 to 6 in the case of the cation exchanger and from 6 to 8 in the case of the anion exchanger. The solvents used are the usual buffer solutions. The glucose oxidase is advantageously eluted from the exchangers with a salt solution using a concentration gradient. For this purpose, all physiologically acceptable salts are suitable, especially sodium chloride, the gradients applied ranging from about 0 to 0.5 mol. It is advantageous to add a suitable buffer substance to the salt solution, for example an acetate or a phosphate in a concentration of about 0.005 to 0.1 mol.

The eluate running down is collected in fractions. The fractions containing the glucose oxidase which are generally obtained in the first elution step (absorption at 280 nm) are combined. If desired, they can be concentrated by ultra-filtration, dialyzed once more and finally lyophilized.

The composition prepared according to the invention is homogeneous as shown by electrophoresis and ultracentrifugal analysis.

The determination of the glucose oxidase is effected by converting glucose and oxygen into gluconolactone and hydrogen peroxide. The hydrogen peroxide so obtained can be determined either by iodometry or by colorimetry (according to Bergmeyer, H.U. Methoden der Enzymatischen Analyse, Vol.1, page 416, 2nd edition, 1970, published by Chemie-Weindheim).

One glucose oxidase unit corresponds to the amount of enzyme by which 1 $\mu$ mole of glucose is reacted per minute, the substrate being saturated.

The activity of the catalase was evaluated according to Bergmeyer, H.U. (Methoden der Enzymatischen Analyse, vol. 1, page 645, 2nd edition, 1970, published by Chemie-Weinheim) by determining the time which is required for the decrease of the hydrogen peroxide concentration from 500 to 450 extinction units at 240 nm.

A catalase unit corresponds to the enzyme amount which sets free half of the peroxide oxygen contained in a $H_2O_2$-solution of any concentration (about $10^{116}$ $^2M$) at 25°C within 100 sec.

To precipitate the glucose oxidase the acridine compound is used in an amount which corresponds to 0.5 – 3 g, calculated on 10 g of glucose oxidase.

The following example illustrates the invention.

EXAMPLE 10 g of glucose oxidase of *Aspergillus niger* available in commerce and having a glucose oxidase activity of 15 units/mg of protein and a catalase activity of 1 unit/mg of protein were dissolved to give a 10 % solution in 0.01 molar sodium phosphate of pH 6 prepared from phosphoric acid solution and sodium hydroxide and dialyzed against 0.01 molar sodium phosphate of pH 6. The solution was precipitated with a 3 % aqueous solution of diaminoethoxyacridine lactate, 1 mg of diaminoethoxyacridine lactate being used per 10 mg of protein. The solution was allowed to dwell at 4°C for 15 hours. The diaminoethoxyacridine lactate-protein complex which had precipitated contained the glucose oxidase. It was isolated by centrifuging and the glucose oxidase was set free by suspending the precipitate in 35 ml of 5 % sodium chloride solution.

The solution containing the glucose oxidase was separated from the sparingly soluble chloride of the acridine base by filtration. The solution containing the enzyme was dialyzed against distilled water and then against 0.008 molar sodium acetate of pH 4 at 4°C. The resulting product was subjected to chromatography using sulfethyl(SE)-Sephadex (registered trade mark) C-50 (Deutsche Pharmacia, Frankfurt/M), the ion exchanger having been equilibrated by means of 0.008 molar sodium acetate of pH 4. The glucose oxidase was eluted using a linear gradient of from 0 to 0.3 molar sodium chloride in 0.008 sodium acetate of pH 4. The first elution peak contained the glucose oxidase. The solution was adjusted with sodium hydroxide to pH 6 and dialyzed against 0.01 molar sodium phosphate of pH 6, followed by chromatography with diethylaminoethyl(DEAE)-Sephadex A-50 (registered trade mark) (Deutsche Pharmacia, Frankfurt/M), the ion exchanger having been equilibrated with 0.01 molar sodium phosphate of pH 6. The glucose oxidase was eluted using a gradient of from 0 to 0.3 molar sodium chloride in 0.01 molar sodium phosphate of pH 6. The first elution peak contained the catalase, the second one contained the glucose oxidase.

The DEAE-Sephadex A-50-chromatography was repeated once more. The glucose oxidase fraction was concentrated by ultrafiltration up to a protein content of 2 %, dialyzed against 0.02 molar sodium phosphate solution of pH 6 and lyophilized.

The specific glucose oxidase activity of the end product was 255 units/mg of protein, the yield of activity was 45 %. The glucose oxidase obtained according to the invention contained 0.08 unit catalase/mg of protein.

Similar good results were obtained when the adsorption and the elution of the enzyme were carried out at the ion exchangers by degrees according to the so-called batch process. If necessary, the glucose oxidase could be crystallized after purification.

According to the purification process described in example 1 glucose oxidase poor in catalase could likewise be obtained from glucose oxidase compositions of *Penicillium notatum* and other molds available in commerce.

I claim:

1. A process for obtaining glucose oxidase poor in catalase which comprises precipitating a prepurified glucose oxidase composition with a water-soluble salt of an acridine base, and subsequently purifying it by chromatography on a cation exchanger and an anion exchanger.

2. A process as defined in claim 1 in which the cation exchanger is one having functional sulfoethyl groups and the ion exchanger is one having functional diethylamino groups.

3. A process as claimed in claim 1 wherein said water-soluble salt of an acridine base is diaminoethoxyacridine lactate.

4. A process as claimed in claim 1 wherein said prepurified glucose oxidase composition is derived from a mold.

5. A process as claimed in claim 4 wherein said mold is *Aspergillus niger*.

6. A process as claimed in claim 4 wherein said mold is *Penicillium notatum*.

7. Glucose oxidase poor in catalase, prepared by the process of claim 1, containing more than 250 units/mg of protein of glucose oxidase activity and less than 0.1 unit/mg of protein of catalase activity.

* * * * *